United States Patent [19]

Horn et al.

[11] Patent Number: 5,045,623

[45] Date of Patent: Sep. 3, 1991

[54] TRANSPARENT, STEAM STERILIZABLE, NONCELLULAR POLYURETHANE COMPOSITIONS A PROCESS FOR THEIR PREPARATION AND THEIR USE ESPECIALLY FOR MEDICINAL ARTICLES

[75] Inventors: Peter Horn, Heidelberg; Werner Hinz, Frankenthal; Walter Heckmann, Weinheim; Falko Ramsteiner, Ludwigshafen; Friedrich Gerold, Haar, all of Fed. Rep. of Germany

[73] Assignee: BASF Aktiengesellschaft, Ludwigshafen, Fed. Rep. of Germany

[21] Appl. No.: 564,224

[22] Filed: Aug. 8, 1990

[30] Foreign Application Priority Data

Aug. 18, 1989 [DE] Fed. Rep. of Germany ....... 3927244

[51] Int. Cl.$^5$ .............................................. C08G 18/10
[52] U.S. Cl. ........................................ 528/60; 528/65; 528/66
[58] Field of Search ............................. 528/60, 65, 66

[56] References Cited

U.S. PATENT DOCUMENTS

| | | | |
|---|---|---|---|
| 3,692,094 | 6/1976 | Davis et al. | 210/321 |
| 4,118,411 | 10/1978 | Reiff et al. | 260/453 |
| 4,170,559 | 10/1979 | Kroplinski et al. | 210/321 |
| 4,224,164 | 9/1980 | Brauer et al. | 210/321 |
| 4,254,176 | 3/1981 | Muller et al. | 528/65 |
| 4,478,960 | 10/1984 | Buethe et al. | 521/160 |
| 4,629,768 | 12/1986 | Hire et al. | 525/458 |
| 4,814,103 | 3/1989 | Potter et al. | 252/182.22 |

Primary Examiner—Maurice J. Welsh
Attorney, Agent, or Firm—William G. Conger

[57] ABSTRACT

The present invention relates to transparent essentially non-cellular polyurethane casting compositions that are sterilizable with superheated steam which are prepared by reacting:

(A) modified diphenylmethane diisocyanates (A) liquid at 23° C. obtained by reacting
  (A1) 4,4'-diphenylmethane diisocyanate or
  (A2) 2,4'-diphenylmethane diisocyanate or
  (A3) a diphenylmethane diisocyanate mixture with
  (A4) at least one polyoxypropylene polyol and/or
  (A5) at least one polyoxypropylene polyoxyethylene polyol containing 1 to 80 weight percent of ethylene oxide units whereby (A4) and (A5) have a functionality of 4 to 8 and a hydroxyl number of 150 to 500 and are obtained while using sucrose and/or preferably sorbitol as initiator molecules
  (A6) a mixture of (A4) and/or (A5) and at least one polyoxypropylene polyol and/or polyoxyethylene polyol initiated with glycerine and/or trimethylolpropane in a NCO:OH group ratio of 2.5:1 to 15:1 with (B) at least one compound having at least reactive hydrogen atoms which preferably contains no primary, secondary or tertiary amino groups in bonded form in the presence of or absence of (C) catalysts.

The present invention also relates to a process for the preparation of polyurethane casting compositions and their use for medical-technical articles.

14 Claims, No Drawings

TRANSPARENT, STEAM STERILIZABLE, NONCELLULAR POLYURETHANE COMPOSITIONS A PROCESS FOR THEIR PREPARATION AND THEIR USE ESPECIALLY FOR MEDICINAL ARTICLES

The invention relates to transparent, substantially compact polyurethane (hereinafter also abbreviated as PU) casting compositions that are sterilizable with superheated steam, and which are prepared by the reaction of:

A1) 4,4'-diphenylmethane diisocyanate; or
A2) 2,4'-diphenylmethane diisocyanate; or
A3) a diphenylmethane diisocyanate mixture which based on 100 parts by weight comprises:
   A31) 20 to 90 parts by weight of 4,4'-diphenylmethane diisocyanate;
   A32) 80 to 8 parts by weight of 2,4'-diphenylmethane diisocyanate; and,
   A33) 0 to 15 parts by weight of 2,2'-diphenylmethane diisocyanate;
with:
A4) at least one polyoxypropylene polyol having an average functionality of from 4 to 8 and a hydroxyl number of from 230 to 500 obtained while using sorbitol, sucrose, or a mixture thereof as an initiator molecule whereby additionally, water, propylene glycol, glycerine, or mixtures of at least two of the aforesaid are used as costarters, or
A5) at least one polyoxypropylene-polyoxyethylenepolyol initiated with sucrose, or more preferably sorbitol having 1 to 80 weight percent of ethylene oxide units polymerized in situ, based on the total weight and having a hydroxyl number of 150 to 500 or
A6) a polyoxyalkylene-polyol mixture having an average functionality of at least 4 prepared from one of the aforesaid sucrose- or sorbitol-polyoxypropylene polyols (A4) or the sucrose- or sorbitolpolyoxypropylene-polyoxyethylene-polyols (A5) and from a polyoxypropylene-polyol and/or a polyoxyethylene polyol having a hydroxyl member of from 350 to 950, obtained by reacting glycerine, trimethylolpropane, or a mixture thereof with 1,2-propylene oxide or ethylene oxide in a mole ratio of 1:1 to 1:8,
or mixtures of at least two of said components (A4) through (A6), in a NCO to OH group ratio of from 2.5:1 to 15:1; with
B) at least one compound having at least two reactive hydrogen atoms, which preferably contains no primary, secondary or tertiary amino groups in bonded form;
in the presence or absence of:
C) catalysts.

PU casting systems are known and are summarily described for instance in the plastics handbook, "Polyurethane" [Polyurethanes], Vol. 7, 2nd Edition, 1983, pp. 392 ff, edited by Dr. G. Oertel, published by Carl Hanser Verlag, Munich and Vienna.

The use of PU casting compositions to produce molded articles for medical-technical equipment, in particular as an embedding material for embedding hollow fibers in dialyzers, is likewise not new, and is recommended as advantageous because of the easy handling of PU casting compositions and their low shrinkage during the curing process. For example, the following PU formulations are known, particularly for embedding hollow fibers:

U.S. Pat. No. 3,962,094 describes catalyst-free casting compositions, comprising ricinoleic-4,4'-MDI, ricinoleic toluene diisocyanate or ricinoleic phenylene diisocyanate prepolymers with terminally positioned NCO groups and a cross-linking agent, which contains ricinous oil and/or an ester of an at least tetravalent alcohol and an aliphatic carboxylic acid having hydroxy or epoxy groups and at least 12 carbon atoms.

According to West German Patent Disclosure A 2 749 491 (equivalent to U.S. Pat. No. 4,170,559), the catalyst-free casting compositions comprise a prepolymer prepared from ricinous oil and polyoxypropylene glycol as well as 4,4'-MDI, and a cross-linking agent based on an ester of a multivalent alcohol having 2 or 3 hydroxyl groups and an aliphatic carboxylic acid with at least 12 carbon atoms and one or more hydroxyl and/or epoxy groups. The following suitable polyisocyanates for preparing the prepolymers are also named: 2,4- and 2,6-toluene diisocyanate or phenylene diisocyanate. As cross-linking agents, monoesters and/or diesters of ethylene glycol and ricinoleic acid, trimethylol propane or trimethylol ethane are also possible.

Physiologically unobjectionable PU molding materials, particular for embedding hollow fibers in dialyzers, are prepared according to East German Patent 251 565 by the reaction of highly reactive, low-viscosity, storable mixed prepolymers, comprising solid, highly reactive aromatic diisocyanates and less-reactive liquid diisocyanates in a ratio by weight of 1:5 to 5:1 and polyols, with polyols selected from the group of ricinous oil and/or its transesterification products, high-purity polyesters and polyoxytetramethylene glycol. PU casting compositions comprising a PU prepolymer having terminally positioned isocyanate groups and a polyol mixture containing N,N,N',N'-tetrakis(2-hydroxypropyl)-ethylenediamine are the subject of U.S. Pat. No. 4,224,164. For preparing PU casting compositions for electrical equipment, mixtures of from 10 to 60% by weight of an ricinoleic acid ester and 90 to 40% by weight of a $C_2$- to $C_6$-hydrocarbon polymer with at least one hydroxyl group are used as the polyol component, according to U.S. Pat. No. 4,742,112. Two-component PU formulations that are not cytotoxic in the cured state and are suitable as casting compositions for separating apparatus, according to West German Patent Disclosure 3 048 529 (U.S. Pat. No. 4,332,927), comprise at least one NCO-terminated prepolymer, at least one polyol, and a catalytically active quantity of a dicarboxylated dialkyl tin compound. PU casting compositions catalyzed with tinsulfur compounds for embedding cellulose hollow fibers in dialyzers are described in East German Patent 155 777.

The above-named PU casting compositions can be processed into medical-technical equipment and/or molded parts for such equipment and can be sterilized before use with ethylene oxide and/or with gamma rays. A disadvantage of this type of sterilization, however, is that residual traces of ethylene oxide can trigger allergies in some patients, and the gamma rays can form unidentifiable fission products, so that a certain risk to the patient's health from the dialysis cannot be entirely precluded. Yet, the casting compositions known from the prior art are not sufficiently temperature- and chemical-resistant, and so cannot be subjected to superheated steam sterilization at a temperature of 121° C. over a time period of 20 minutes.

Another serious disadvantage is that conventional PU casting compositions cannot be processed with every type of fiber. For example, cellulose fibers are attacked and damaged by PU casting compositions based on ricinous oil. In addition, when processing state of the art PU casting composition systems many difficulties arise during the course of production. The casting compositions made can be cut directly after casting and within about 30 minutes thereafter, however, they postcure very quickly so that molded articles especially dialysis filters no longer can be cut after 24 hours. This adverse behavior leads especially to production problems and product losses on the working end. If PU formulations are used to prepare PU casting compositions which as starting components contain in bonded form primary, secondary and/or tertiary amino groups and reactive hydrogen atoms, then the resulting casting compositions are instable to sterilization with peracetic acid. On the other hand, PU casting compositions based on ricinous oil oxidizes on the double bonds and form toxic aliphatic epoxides. Since conventional sterilization methods are generally used which are done with 3 weight percent of peracetic acid and 30 weight percent of hydrogen peroxide the resulting acidic acid immediately reoxidizes with the hydrogen peroxide into peracetic acid and the formation of epoxide is not visible.

The object of the present invention is to develop transparent, substantially compact PU casting compositions that can be sterilized with superheated steam, for medical-technical articles, which possess none of the aforesaid disadvantages. PU casting formulations suitable therefore are hopefully shrinkage free when processed; the resulting casting compositions should not post cure and they are predominantly resistant against percarboxylic acids.

Unexpectedly, this object was met by using room temperature liquid diphenylmethane diisocyanates specially modified with urethane groups or diphenylmethane diisocyanate isomeric mixtures preferably combined with NCO group reactive, at least difunctional compounds which contain no amino groups in bonded form, for the preparation of the PU casting compositions.

Hence, the subject of the invention is transparent, substantially compact PU casting compositions that are sterilizable with superheated steam, which are prepared by the reaction of A) modified diphenylmethane diisocyanates, with
B) at least one compound having at least two reactive hydrogen atoms in the presence or absence of
C) catalysts, and are characterized in that the modified diphenylmethane diisocyanate quasi prepolymer are prepared by the reaction of A1) 4,4'-diphenylmethane diisocyanate; or
A2) 2,4'-diphenylmethane diisocyanate; or
A3) a diphenylmethane diisocyanate isomeric mixture, with:
A4) at least one polyoxypropylene polyol having an average functionality of from 4 to 8, more preferably 4 to 6 and a hydroxyl number of from 230 to 500, more preferably 250 to 480 prepared while using sorbitol, sucrose, or a mixtures of sorbitol and sucrose as initiator molecules whereby additionally water, propylene glycol, glycerine, or mixtures of at least two of the aforesaid are used as a costarter;

A5) at least one polyoxypropylene-polyoxyethylenepolyol initiated with sucrose, or more preferably sorbitol having 1 to 80 weight percent more preferably 10 to 70 weight percent of ethylene oxide units polymerized in situ, based on the total weight and having a hydroxyl number of 150 to 500, more preferably 230 to 300; or A6) a polyoxyalkylene polyol mixture having an average functionality of at least 4; more preferably 4 to 6, prepared from at least one of the aforesaid sucrose- or sorbitol-polyoxypropylene polyols (A4) or the sucrose- or the sorbitol- polyoxypropylene-polyoxyethylene-polyols (A5) and from a polyoxypropylene-polyol and/or a polyoxyethylene polyol having a hydroxyl member of from 350 to 950 more preferably 380 to 600 prepared by reacting glycerine, trimethylolpropane, or a mixture of glycerine and trimethylolpropane with 1,2-propylene oxide or ethylene oxide in a mole ratio of 1:1 to 1:8, more preferably 1:1 to 1:3 or mixtures of at least two of said components (A4) through (A6), in a NCO to OH group ratio of from 2.5:1 to 15:1, more preferably 5:1 to 10:1.

The invention also relates to a process for preparing the transparent, substantially compact polyurethane casting compositions that are sterilizable by superheated steam of claim 12, as well as to the use of the PU casting compositions for embedding hollow fibers preferably of polysulfones, polycarbonates or cellulose in dialyzers, for producing medical-technical articles, and also for bonding bioceramic coatings to endoprostheses of claim 14.

Since the prior art mentions not only 1,5-naphthalene diisocyanate, toluene diisocyanates and phenylene diisocyanates but also 4,4'-MDI, where the polyisocyanates are suitably made to react in the form of prepolymers, as suitable polyisocyanates for preparing the PU casting compositions, in particular for embedding hollow fibers in dialyzers, and since in this process polyurethanes that are sterilizable by superheated steam are not obtained, it was unexpected and unforeseeable that the selected, special MDI-isomer mixture, modified with the special polyoxypropylene triols in specific quantitative ratios, lend the cured PU casting compositions prepared from it an increased temperature resistance and improved hydrolysis resistance, so that the medical-technical articles can be sterilized in superheated steam without any problem.

It is also advantageous that by using the modified MDI's of the present invention the maximum curing temperature of the reaction of components A with B in the presence of or preferably in the absence of C is clearly lowered so that when preparing the PU casting compositions one does not obtain a temperature of 127° and greater, measured at the center point of a conically flared, open 300 ml beaker of hard paper (made by the Uniplast Company, 7417 Dlling, FRG) with a bottom diameter of approximately 53 mm and an opening of approximately 75 mm, into which 100 g of reaction mixture are poured, because the hollow fibers made of the aforesaid materials are damaged at a temperature of 127° C. or greater. Selected components A and B assure quick curing of the PU casting composition without impairing its ability to be cut after 24 hours. Through the preferred use of B compounds which, except for hydroxyl groups contain no other groups reactive with NCO groups, especially, no primary, secondary and/or tertiary amino groups in bonded form, PU casting compositions are also obtained which are stable against percarboxylic acid so that molded articles from such PU casting compositions can be sterilized with peracetic acid. By using polyoxypropylene polyoxyethylene polyols containing up to 80 weight percent, more preferably 10 to 80 weight percent of ethylene oxide units, as starting component B, one obtains essentially non-foaming PU casting formulations which need not or need only be briefly degassed before processing and in turn this leads to a substantial reduction in processing costs.

A) The modified MDI's (A) useable according to the invention suitably have a viscosity at 23° C. of 100 to 8000 mPas, more preferably 500 to 3000 mPas and a NCO content of 17 to 29 weight percent, more preferably 19 to 26 weight percent based on the total weight, and are prepared by otherwise conventional processes by reacting 4,4'-MDI (A1) or 2,4'-MDI (A2) or MDI isomeric mixtures (A3) with at least one polyoxypropylene polyol (A4) or with at least on polyoxypropylene polyoxyethylene polyol (A5) or a mixture (A6) from A4 and/or A5 and at least one polyoxypropylene polyol and/or polyoxyethylene polyol initiated with glycerine and/or trimethylolpropane at a temperature of suitably 60° to 100° C., more preferably 70° to 90° C. and a reaction time of 0.5 to 3 hours, more preferably 1 to 2 hours.

MDI isomeric mixtures (A3) typically used are those which based on 100 parts by weight comprise:
A31) 20 to 90 parts by weight, more preferably 50 to 82 parts by weight of 4,4'-MDI;
A32) 80 to 8 parts by weight, more preferably 50 to 8 parts by weight of 2,4'-MDI;
A33) 0 to 5 parts by weight, more preferably 0 to 3 parts by weight of 2,2'-MDI.

Typical polyoxypropylene polyols (A4) are: polyoxypropylene polyols initiated with sucrose, polyoxypropylene polyols initiated with sorbitol or mixtures of the aforesaid polyoxypropylene polyoxyethylene polyols. Polyoxypropylene polyols are equally well suited prepared while using a mixture of sucrose and sorbitol as an initiator molecule whereby the weight ratio of sucrose to sorbitol can be varied within wide limits. Preferably used is a polyoxypropylene polyol initiated with sorbitol having a hydroxyl number of 250 to 380.

In place of sucrose and/or preferably sorbitol as initiator molecules, when preparing the polyoxypropylene polyols, mixtures of the aforesaid initiator molecules and at least one costarter selected from the group consisting of water, propylene glycol and glycerine can be used provided that the costarter is only used in such a quantity so that the functionality of the resulting polyoxypropylene polyols does not fall below 4. If costarters are used for the preparation of polyoxypropylene polyols (A4), then typically these are used in such quantities so that per mole of sucrose and/or sorbitol a maximum of two moles, more preferably 0.1 to 1.8 moles of costarter is present in the starter mixture.

In place of the aforesaid polyoxypropylene polyols (A4), or mixtures thereof, as already indicated, polyoxypropylene polyoxyethylene polyols (A5) initiated with sucrose and/or preferably sorbitol containing 1 to 80 weight percent of polymerized ethylene oxide units could also be used. Also suitable are polyoxyalkylene polyol mixtures (A6) having an average functionality of at least 4, more preferably 4 to 8 and most preferably 4 to 6, having a hydroxyl number of 230 to 500, more preferably 240 to 480 which typically comprise 1 to 40 parts by weight 3 to 30 parts by weight of at least one of the aforesaid sucrose-and/or sorbitol-polyoxypropylene (A4)-polyols or sucrose-and/or sorbitol-polyoxypropylene-polyoxyethylene-polyols (A5) and 3 to 30 parts by weight, more preferably 5 to 25 parts by weight of at least one of the above-described polyoxypropylene polyols and/or polyoxyethylene polyols based on glycerin and/or trimethylolpropane as initiator molecules.

(B) As compounds (B) having at least two reactive hydrogen atoms, mixtures are preferably used that comprise: (B1) at least one polyhydroxyl compound having a molecular weight of from 1000 to 8500 and a functionality of 2 to 8; (B2) at least one lower-molecular weight divalent alcohol, ester and/or ether -bridged glycol; and (B3) at least one cross-linking agent containing hydroxyl groups, the agent having a hydroxyl number of from 100 to 1900 and a functionality of from 3 to 8.

B1) As polyhydroxyl compounds (B1) having a molecular weight of 1000 to 8500, preferably from 1500 to 5600 and in particular from 1800 to 4000 and a functionality of 2 to 8, preferably 2 to 4 and in particular 2 and/or 3, polyesterols and in particular polyetherols are preferably suitable. However, other polymers containing hydroxyl groups with ether or ester groups as bridge members are also possible, e.g., polyacetals, such as polyoxymethylenes and above all water-insoluble methylals, such as polybutanediol methylol and polyhexanediol methylol, and polycarbonates, particularly those prepared by transesterification from diphenyl carbonate and 1,6-hexanediol. The polyhydroxyl compounds named can be used as single components or in the form of mixtures.

Suitable polyesterols can be prepared for instance from dicarboxylic acids having from 2 to 12 and preferably 4 to 6 carbon atoms and multivalent alcohols. Examples of possible dicarboxylic acids are: aliphatic dicarboxylic acids, such as succinic acid, glutaric acid, adipinic acid, suberic acid, azelaic acid and sebacic acid, and aromatic dicarboxylic acids such as phthalic acid, isophthalic acid and terephthalic acid. The dicarboxylic acids can be used individually or as mixtures, for instance in the form of a mixture of succinic, glutaric and adipinic acid. For preparing the polyesterols, it may optionally be advantageous to use, instead of the dicarboxylic acids, the corresponding dicarboxylic acid derivatives, such as dicarboxylic acid monoesters or diesters having from 1 to 4 carbon atoms in the alcohol radical, dicarboxylic acid anhydrides or dicarboxylic acid dichlorides. Examples of multivalent alcohols are glycols having from 2 to 10 and preferably 2 to 6 carbon atoms, such as ethylene glycol, diethylene glycol, 1,4-butanediol, 1,5-pentanediol, 1,6-hexanediol, 1,10-decanediol, 2,2-dimethyl-1,3-propanediol, 1,3-propanediol and dipropylene glycol. Depending on the properties desired, the multivalent alcohols can be used along with or optionally in mixtures with one another.

Also suitable are esters of the carbonic acid with the aforementioned diols, particularly those having from 4 to 6 carbon atoms, such as 1,4-butanediol and/or 1,6-hexanediol; condensation products of omega-hydroxycarboxylic acids, such as omega-hydroxycaproic acid; and preferably polymerization products of lactones, such as optionally substituted omega-caprolactones.

As polyesterols, the following are preferably used: ethanediol polyadipates, 1,4-butanediol polyadipates, ethanediol-1,4-butanediol polyadipates, 1,6-hexanediol neopentylglycol polyadipates, 1,6-hexanediol-1,4-butanediol polyadipates, and polycaprolactones.

The polyesterols have molecular weights of 1500 to 5600, preferably 1800 to 3500.

The polyetherols preferably used in particular may be prepared by known processes, such as anionic polymerization with alkali hydroxides, such as sodium hydroxide or potassium hydroxide, or alkali alcoholates, such as sodium methylate, sodium or potassium methylate or potassium isopropylate as catalysts, with the addition of at least one initiator molecule that contains from 2–8 and preferably 2–4 reactive hydrogen atoms in bonded form, or by cationic polymerization from one or more alkylene oxides having from 2 to 4 carbon atoms in the alkylene radical, with Lewis acids such as antimony pentachloride, boron fluoride etherate and others, or fuller's earth as catalysts.

Suitable alkylene oxides are for instance tetrahydrofuran, 1,3-propylene oxide, 1,2- or 2,3-butylene oxide, and preferably ethylene oxide and 1,2-propylene oxide. The alkylene oxides can be used individually, in alternation with one another or as mixtures. Possible initiator molecules include the following, for example: water; organic dicarboxylic acids, such as succinic acid, adipinic acid and/or glutaric acid; and preferably divalent or trivalent alcohols optionally containing ether bridges in bonded form, such as ethanediol, 1,2- and 1,3-propanediol, 1,4-butanediol, diethylene glycol, 1,5-pentanediol, 1,6-hexanediol, dipropylene glycol, 2-methyl-1,5-pentanediol and 2-ethyl-1,4-butanediol, glycerine, trimethylol propane, pentaerythritol, sorbitol and saccharose. The initiator molecules can be used individually or as mixtures.

Preferably, polyetherols of 1,2-propylene oxide and ethylene oxide are used, in which more than 50%, and preferably 60–80% of the OH groups are primary hydroxyl groups, and in which at least some of the ethylene oxide is disposed as a terminally positioned block. Such polyetherols can be obtained by polymerizing the 1,2-propylene oxide first to the initiator molecules, and then the ethylene oxide, or first copolymerizing all of the 1,2-propylene oxide in a mixture with part of the ethylene oxide and then subsequently polymerizing the rest of the ethylene oxide to it, or incrementally, first polymerizing part of the ethylene oxide, then all of the 1,2-propylene oxide, and finally the rest of the ethylene oxide to the initiator molecules.

Also, polyoxytetramethylene glycols, advantageously those having molecular weights of from 1000 to 3000, are particularly suitable.

The suitable polyetherols have molecular weights of from 1000 to 8500, preferably 1500 to 5600, and in particular 1800 to 5000. They can be used both individually and in the form of mixtures with one another.

Possible polyacetals containing hydroxyl groups are for instance those that can be prepared from glycols, such as diethylene glycol, triethylene glycol, 4,4'-dihydroxyethoxy-diphenyldimethylmethane, hexanediol and formaldehyde. Suitable polyacetals can also be prepared by polymerization of cyclic acetals.

Polycarbonates having hydroxyl groups that are possible include those of the type known per se that can be prepared for instance by the reaction of diols, such as 1,3-propanediol, 1,4-butanediol and/or 1,6-hexanediol, diethylene glycol, triethylene glycol or tetraethylene glycol with diarylcarbonates, such as diphenylcarbonates, or phosgene.

B2) As low-molecular divalent alcohols, the following glycols containing ester or ether groups as bridge members in bonded form are for instance possible: alkanediols having from 2–10 carbon atoms, preferably 2–6 carbon atoms, such as ethanediol, 1,2- or 1,3-propanediol, 2,2-dimethyl propanediol, 1,4-, 1,3-, or 2,3-butanediol, 1,5- or 2,5-pentanediol, 1,6-hexanediol, 2,2,5-trimethyl- or 2,2,5,5-tetramethyl-1,6-hexanediol; cycloalkanediols and alkylcycloalkanediols having from 6 to 19 carbon atoms, preferably 6 to 15 carbon atoms, such as 1,4-dihydroxycyclohexane, 1-hydroxymethyl-4-hydroxycyclohexane, 1,4-bis-(hydroxymethyl)-cyclohexane, 4,4'-dihydroxy-2,2-dicyclohexylmethane or -propane; glycols containing ester bridges in bonded form, such as 3-hydroxy-2,2-dimethylpropionic acid-2-hydroxyethylester, terephthalic acid-bisethylene glycol or 1,4-butanediol; and glycols containing ether bridges in bonded form having molecular weights up to 378, such as hydroxyalkylene ether of hydroquinone, such as 1,4-di-(beta-hydroxyethyl-hydroquinone; oxyalkylene glycol having from 4-8 carbon atoms, such as diethylene, dipropylene or dibutylene glycol; as well as the corresponding higher-molecular oligomers thereof, such as dioxyethylene, trioxyethylene, dioxypropylene, trioxypropylene, dioxybutylene, trioxybutylene or tetraoxybutylene glycol and ethoxylated 4,4'-dihydroxydiphenyl-2,2-propanes having molecular weights from 316 to 4011. The dihydroxy compounds from the group of alkane-, cycloalkane-, alkylcycloalkyldiols, the corresponding glycols containing ester or ether bridges, in bonded form, and the 4,4'-dihydroxydiphenyl-2,2-propanes can be used individually or as mixtures.

B3) As cross-linking agents containing hydroxyl groups having a hydroxyl number of 100 to 1900 and a functionality of 3 to 8, the following are preferably used: low-molecular tri- to octavalent, preferably tri- to tetravalent alcohols; the corresponding polyols containing in bonded form ester groups as bridge members and the polyoxyalkylene polyols having hydroxyl numbers of 100 to 1900 initiated with lower molecular weight tri- to octavalent alcohols. Typical trivalent to higher valent alcohols are: glycerine, trimethylolpropane, pentaerythritol, 2,2,6,6-tetrahydroxymethyl-4-oxa-1,7-heptanediol (dipentaerythritol), tripentaerythritol, 3,3,7,7-tetrahydroxymethyl-5-oxanone (di-trimethylol propane) and sorbitol.

When preparing the polyoxyalkylene polyols having hydroxyl numbers of 100 to 1900, used are the aforesaid tri to octavalent alcohols as initiator molecules and ethylene oxide and/or 1,2-propylene oxide.

Hydroxyl group containing crosslinkers (B3) which have also proven themselves and therefore are preferably used are: polyoxypropylene polyols (A4), polyoxypropylene polyoxyethylene polyols (A5) or the polyoxyalkylene mixtures (A6) comprising (A4) and/or (A5) and at least one polyoxypropylene polyol and/or polyoxyethylene polyol initiated with glycerine and/or trimethylolpropane relevant to the present invention for modifying the 4,4'-MDI, 2,4'-MDI or the MDI isomeric mixtures. Most preferred here are compounds having at least 2 reactive hydrogen atoms (B) which contain no primary, secondary or tertiary amino groups in bonded form.

The polyhydroxyl compounds B1-B3 are suitably used in such quantities that the mixture B comprises 1.0 moles of B1, 0.01 to 48 moles and preferably 2 to 20 moles of B2, and 0.01 to 32 moles and preferably 1.3 to 7 moles of B3.

It may optionally be advantageous, particularly when PU casting compositions with excellent surface quality are required, to use the following as a further constituent component (D), in addition to the aforementioned polyhydroxyl compounds B1-B3: glycerine monooleate, glycerine dioleate or mixtures thereof. If on the other hand one uses as starting component (D), additionally block polyoxypropylene polyoxyethylene glycols containing 1 to 80 weight percent, more preferably 10 to 80 weight percent of ethylene oxide units and having a molecular weight of 1500 to 8000, more preferably 2000 to 6000 to obtain practically nonfoaming PU casting formulations, then such compounds can be obtained for example, having the trade name Pluronic®PE from BASF Corporation. If glycerine monooleates and/or glycerine dioleates and/or block polyoxypropylene polyoxyethylene polyols are used, then typically these are used in quantities of from 0.1 to 5 weight percent, more preferably 1 to 4 weight percent based on the total weight of (A) and (B).

The preparation of the PU casting compositions can be performed in the presence or absence of catalysts. As suitable catalysts, dialkylcarboxylates such as dibutyl tin diacetate, dibutyl tin dilaurate and dicarboxylated dialkyl tin compounds of the kind described in West German Patent A 3 048 529 have proven themselves. If catalysts are used, they are typically used in a quantity of from 0.001 to 0.2 parts by weight, preferably 0.005 to 0.015 parts by weight, per 100 parts by weight of the constituent component (B).

To prepare the PU casting compounds, the modified MDI's (A) and compounds having at least two reactive hydrogen atoms (B) and optionally the constituent component (D) are made to react in the presence or absence of the catalysts (C), in such quantities that the equivalence ratio of NCO groups of the modified MDI's (A) to the sum of the reactive hydrogen atoms of component (B) and optionally (D) is 1:0.9 to 1.3, preferably 1:0.95 to 1.2, and in particular 1:0.98 to 1.1. To this end, the substantially completely degassed starting components are intensively mixed at temperatures of suitably 18° to 70° C., preferably 22° to 60° C., the reaction mixture is placed in a suitable molding tool, and is allowed to cure for a period of time of from 0.3 to 4 hours, preferably from 1 to 3 hours.

As already explained, the transparent, substantially compact PU casting compositions sterilizable with superheated steam which contain no compounds with primary, secondary or tertiary amino groups in bonded form are used in particular for embedding hollow fibers, preferably polysulfone, polycarbonate or cellulose hollow fibers in dialyzers; the dialysis equipment, and in particular the envelope for the dialysis filter suitably comprises a polycarbonate based on bisphenol A.

The PU casting compositions according to the invention are also suitable for producing medical-technical articles and for bonding bioceramic coatings to endoprostheses.

The PU casting compositions are nontoxic, transparent, exhibit no interaction with the hollow fibers, have pronounced adhesion to the polycarbonate, and can be cut well without destroying the embedded hollow fibers. Another essential factor for the use of the products is that the maximum temperature in curing under the conditions described is below 127° C., and the medical-technical articles can be subjected to superheated steam sterilization, and subsequent drying with an air stream heated to 80° C. without damage to the cured PU casting composition or to its adhesion to the polycarbonate housing.

EXAMPLE 1

Preparation of the Modified MDI

In a 6 liter 3 neck flask a MDI mixture comprising:
3130.94 g of 4,4'-MDI and
1050.31 g of 2,4'-MDI
was heated to 80° C. and while stirring a mixture of the following was added drop by drop over a period of 60 minutes:

399.37 g of a mixture having an average functionality of 4.77 and a hydroxyl number of 465 which contained 83 weight percent of a polyoxypropylene polyol having a hydroxyl number of 490 initiated with sorbitol and propylene glycol in a weight ratio of 92:8 and 17 weight percent of a polyoxypropylene polyol having a hydroxyl number of 400 initiated with glycerine; and 399.37 g of a polyoxypropylene polyol having a hydroxyl number of 400 initiated with glycerine.

To complete the reaction it was further stirred 60 minutes at 80° C. The modified MDI obtained had a NCO content of 22.4 weight percent and a viscosity at 25° C. of 1002 mPas.

EXAMPLE 2

Preparation of the PU Casting Composition

A Component:
A mixture of
72.985 parts by weight of a polyoxypropylene (86 weight percent) polyoxyethylene (14 weight percent) triol having a hydroxyl number of 28 initiated with trimethylolpropane, 10.0 parts by weight of 1,4-butanediol, 7.0 parts by weight of a polyoxyethylene triol having a hydroxyl number of 940 initiated with trimethylolpropane, 10.0 parts by weight of a polyoxypropylene (80 weight percent) polyoxyethylene (20 weight percent) polyol having a hydroxyl number of 247 initiated with sorbitol and 0.015 parts by weight of dibutyltin dilaurate.

B Component:

Modified MDI prepared according to Example 1. 100 parts by weight of component A and 84.51 parts by weight of component B were intensively mixed at 23° C., the reaction mixture was poured into a mold and allowed to cure. The gel time was 137 seconds and the maximum reaction temperature was 94.3° C., measured at the center of a conical, open 300 ml hard paper beaker having a bottom diameter of 53 mm and an opening diameter of 75 mm, into which 100 ml of the reaction mixture was added. The PU casting composition was transparent and resistant to steam at 121° C. over a period of more than 20 minutes. The superheated steam sterilization of dialyzers made of polycarbonate equipped with polysulfone hollow fibers prepared by centrifugal casting using the PU casting composition of example 2 caused no damage whatever, even if the dialysis filter was dried with 80° C. hot air following the superheated steam sterilization. The casting composition was stable against a 3 weight percent peracetic acid solution at room temperature for over one week.

EXAMPLE 3

Preparation of the modified MDI

In a 4 liter 3 neck flask a MDI mixture comprising
397.02 g of 4,4'-MDI and
397.02 g of 2,4-MDI
was heated to 60° C. and while stirring
204.96 g a polyoxypropylene (80 weight percent) polyoxyethylene (20 weight percent) polyol having a hydroxyl number of 242
initiated with sorbitol was added drop by drop over a period of 60 minutes. To complete the reaction subsequently stirring occurred for one hour at 80° C. The modified MDI obtained had a NCO content of 22.2 weight percent and a viscosity at 25° C. of 1630 mPas.

EXAMPLE 4

Preparation of the PU Casting Composition

Component A:
A mixture of
69.985 parts by weight of a polyoxypropylene (86 weight percent) polyoxyethylene (14 weight percent) triol having a hydroxyl number of 28 initiated with trimethylolpropane,
10.0 parts by weight of 1,4-butanediol,
7.0 parts by weight of a polyoxyethylene triol having a hydroxyl number of 940 initiated with trimethylolpropane,
10.0 parts by weight of a polyoxypropylene (80 weight percent) polyoxyethylene (20 weight percent) polyol having a hydroxyl number of 242 initiated with sorbitol,
3.0 parts by weight of a polyoxypropylene triol having a hydroxyl number of 555 initiated with glycerine and 0.015 parts by weight of dibutyltin dilaurate.

Component B:
Modified MDI prepared according t example 3. To prepare the PU casting composition 100 parts by weight of the A component and 84.51 parts by weight of the B component were intensively mixed at 23° C., the reaction mixture was poured into an open mold and allowed to cure. The gel time measured here was 152 seconds and the maximum reaction temperature was 86.5° C. reported analogous to example 2.

EXAMPLE 5

Preparation of the PU Casting Composition

Component A:
72.985 parts by weight of a polyoxypropylene (86 weight percent) polyoxyethylene (14 weight percent) triol having a hydroxyl number of 28 initiated with trimethylolpropane,
10 0 parts by weight of 1,4-butanediol,
7.0 parts by weight of a polyoxyethylene triol having a hydroxyl number of 940 prepared from 1 mole of trimethylolpropane as an initiate or molecule and 1.1 moles of ethylene oxide,
10.0 parts by weight of a polyoxypropylene (80 weight percent) polyoxyethylene (20 weight percent) polyol having a hydroxyl number of 243 initiated with sorbitol, and
0.015 parts by weight of dibutyltin dilaurate.

Component B:
Modified MDI prepared according to example 3. 100 parts by weight of the A component and 86.53 parts by weight of the B component were intensively mixed at 23° C., the reaction mixture was poured into a mold and allowed to cure. The gel time was 157 seconds and the maximum reaction temperature was 89° C. measured according to the information in example 2. The PU casting composition was transparent and resistant to steam at 121° C. over a time period of more than 20 minutes. The superheated steam sterilization and subsequent drying using 80° C. hot air of dialyzers made of polycarbonate equipped with polysulfone hollow fibers prepared by a centrifugal casting process while using the PU casting composition of example 5, caused no damage whatsoever. The casting composition was stable against a 3 weight percent peracetic acid solution at room temperature for over one week.

We claim:

1. Transparent, steam sterilizable, essentially non-cellular polyurethane casting compositions, prepared by reacting:
   A) modified diphenylmethane diisocyanates with:
   B) at least one compound having at least two reactive hydrogen atoms;
   in the presence of or absence of:
   C) catalysts; wherein the modified diphenylmethane diisocyanates (A) are prepared by reacting:
   A1) 4,4'-diphenylmethane diisocyanate; or
   A2) 2,4'-diphenylmethane diisocyanate; or
   A3) a diphenylmethane diisocyanate isomeric mixture, with:
   A4) at least one polyoxypropylene polyol having an average functionality of from 4 to 8 and a hydroxyl number of from 230 to 500, prepared while using sorbitol, sucrose, or mixtures of sorbitol and sucrose as initiator molecules whereby additionally water, propylene glycol, glycerine, or mixtures of at least two of the aforesaid are used as a costarter;
   A5) at least one polyoxypropylene-polyoxyethylenepolyol initiated with sucrose, or more preferably sorbitol, containing 1 to 80 weight percent of ethylene oxide units polymerized in situ, based on the total weight, and having a hydroxyl number of from 150 to 500; or,
   A6) a polyoxyalkylene polyol mixture having an average functionality of at least 4, prepared from at least one of the aforesaid sucrose- or sorbitol-polyoxypropylene-polyols (A4), or sucrose- or sorbitol-polyoxypropylene-polyoxyethylene-polyols (A5) and from a polyoxypropylene- and/or polyoxyethylene- polyol having a hydroxyl number of from 350 to 950, prepared by reacting glycerine, trimethylolpropane or a mixture of glycerine and trimethylolpropane with 1,2-propylene oxide or ethylene oxide in a mole ratio of from 1:1 to 1:8;
   or mixtures of at least two of said components (A4) through (A6), in a NCO:OH-group ratio of from 2.5:1 to 15:1.

2. The transparent, steam sterilizable, essentially non-cellular polyurethane casting compositions of claim 1 wherein the modified diphenylmethane diisocyanates have a NCO content of from 17 to 29 weight percent, based on the total weight.

3. The transparent, steam sterilizable, essentially non-cellular polyurethane-casting compositions of claims 1 or 2 wherein the modified diphenylmethane diisocyanates have a viscosity of from 100 to 8000 mPas at 23° C.

4. The transparent, steam sterilizable, essentially non-cellular polyurethane-casting compositions of 1 of claims 1 through 3 wherein the diphenylmethane diisocyanate isomeric mixtures, based on 100 parts by weight, comprise:

A31) 20 to 90 parts by weight of 4,4'-diphenylmethane diisocyanate,

A32) 80 to 8 parts by weight of 2,4'-diphenylmethane diisocyanate; and

A33) 0 to 5 parts by weight of 2,2'-diphenylmethane diisocyanate.

5. The transparent, steam sterilizable, essentially noncellular polyurethane-casting compositions of one of claims 1 through 4 wherein a mixture of the following is used as compounds having at least two reactive hydrogen atoms (B):

B1) at least one polyhydroxyl compound having a molecular weight from 1000 to 8500 and a functionality from 2 to 8;

B2) at least one lower molecular weight divalent alcohol, ester and/or ether-bridge in bonded form-containing glycol and, B3) at least one hydroxyl group containing cross-linker having a hydroxyl number of from 100 to 1900 and a functionality of from 3 to 8.

6. The transparent, steam sterilizable, essentially noncellular polyurethane-casting compositions of one of claims 1 through 5 wherein the compounds having at least two reactive hydrogen atoms (B) have no primary, secondary, or tertiary amino groups in bonded form.

7. The transparent, steam sterilizable, essentially noncellular polyurethane-casting compositions of one of claims 1 through 4 wherein a mixture of the following is used as compounds having at least two reactive hydrogen atoms (B):

B1) at least one polyether polyol having a molecular weight of from 1000 to 8500, and a functionality of from 2 to 8, B2) at least one lower molecular weight dihydroxyl compound selected from the group consisting of alkanediols, cycloalkanediols, alkylcycloalkanediols, the corresponding ester or ether group, as bridge members, in bonded form containing glycols and ethoxylated 4,4'-dihydroxy-2,2-diphenyl propanes having molecular weights of from 316 to 404, B3) at least one cross-linker selected from the group consisting of lower molecular weight tri to octavalent alcohols, the corresponding polyols containing in bonded form ester groups as bridge members and polyoxyalklyene polyols initiated with lower molecular weight tri to octavalent alcohols, having hydroxyl members of from 100 to 1900;

and whereby the (B) compounds contain no primary, secondary, or tertiary nitrogen atoms in bonded form.

8. The transparent, steam sterilizable, essentially noncellular polyurethane casting compositions of 1 of claims 1 through 7 wherein the B mixture comprises:

1.0 moles of (B1);

0.01 to 48 moles of (B2); and 0.01 to 32 moles of (B3).

9. The transparent, steam sterilizable, essentially noncellular polyurethane casting compositions of 1 of claims 1 through 8 wherein additionally, glycerine monooleate and/or glycerine dioleate and/or block-polyoxypropylene-polyoxyethylene glycols comprising 1 to 80 weight percent of ethylene oxide units and having a molecular weight of from 1500 to 8000 are used in their preparation as the D starting component.

10. The transparent, steam sterilizable, essentially noncellular polyurethane casting compositions of 1 of claims 1 through 9 wherein 0.1 to 5 weight percent of (D), based on the total weight of (A) and (B), is used in their preparation.

11. The transparent, steam sterilizable, essentially noncellular polyurethane casting compositions of 1 of claims 1 through 10 wherein they are resistant against sterilization with peracetic acid.

12. A process for the preparation of transparent, steam sterilizable, essentially noncellular polyurethane casting compositions, comprising reacting:

A) modified diphenylmethane diisocyanates with:

B) at least one compound having at least two reactive hydrogen atoms;

in the presence of, or absence of:

C) catalysts;

wherein the modified diphenylmethane diisocyanates (A) have a viscosity of from 100 to 8000 mPas at 23° C., a NCO content of from 17 to 29 weight percent, based on the total weight and are prepared by reacting:

A1) 4,4'-diphenylmethane diisocyanate; or

A2) 2,4'-diphenylmethane diisocyanate; or

A3) a diphenylmethane diisocyanate isomeric mixture with:

A4) at least one polyoxypropylene polyol having an average functionality of from 4 to 8 and a hydroxyl member of from 230 to 500 obtained while using sorbitol, sucrose, or a mixture thereof as an initiator molecule whereby additionally, water, propylene glycol, glycerine, or mixtures of at least two of the aforesaid are used as costarters, A5) at least one polyoxypropylene-polyoxyethylenepolyol initiated with sucrose, or more preferably sorbitol having 1 to 80 weight percent of ethylene oxide units polymerized in situ, based on the total weight and having a hydroxyl number of 150 to 500 or A6) a polyoxyalkylene-polyol mixture having an average functionality of at least 4 prepared from one of the aforesaid sucrose- or sorbitol-polyoxypropylene polyols (A4) or the sucrose- or the sorbitol-polyoxypropylene-polyoxyethylene-polyols (A5) and from a polyoxypropylene-polyol and/or a polyoxyethylene polyol having a hydroxyl member of from 350 to 950, obtained by reacting glycerine, trimethylolpropane, or a mixture thereof with 1,2-propylene oxide or ethylene oxide in a mole ratio of 1:1 to 1:8, or mixtures of at least two of said components (A4) through (A6), in an NCO to OH group ratio of from 2.5:1 to 15:1.

13. The process of claim 12 wherein the diphenylmethane diisocyanate isomeric mixture (A3), based on 100 parts by weight comprises:

A31) 20 to 90 parts by weight of 4,4'-diphenylmethane diisocyanate;

A32) 80 to 8 parts by weight of 2,4'-diphenylmethane diisocyanate; and,

A33) 0 to 15 parts by weight of 2,2'-diphenylmethane diisocyanate.

14. The transparent, steam sterilizable, essentially noncellular polyurethane casting compositions of one of claims 1 through 11 are used to encapsulate hollow fibers preferably of polysulfones, polycarbonates, or cellulose in dialysis equipment, or to prepare medicinal articles and to bind bioceramic films to endoprostheses.

* * * * *